United States Patent
During

(10) Patent No.: US 10,426,746 B2
(45) Date of Patent: *Oct. 1, 2019

(54) METHODS OF TREATING DEVELOPMENTAL DISORDERS WITH BIGUANIDES

(71) Applicant: Ovid Therapeutics Inc., New York, NY (US)

(72) Inventor: Matthew During, Weston, CT (US)

(73) Assignee: OVID THERAPEUTICS INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/157,653

(22) Filed: Oct. 11, 2018

(65) Prior Publication Data

US 2019/0046480 A1    Feb. 14, 2019

Related U.S. Application Data

(63) Continuation of application No. 15/680,417, filed on Aug. 18, 2017, now Pat. No. 10,123,979.

(60) Provisional application No. 62/376,488, filed on Aug. 18, 2016.

(51) Int. Cl.
*A61K 31/155* (2006.01)
*C07C 279/26* (2006.01)

(52) U.S. Cl.
CPC .......... *A61K 31/155* (2013.01); *C07C 279/26* (2013.01)

(58) Field of Classification Search
CPC .............................. A61K 31/55; A61K 31/155
See application file for complete search history.

(56) References Cited

U.S. PATENT DOCUMENTS

| 10,123,979 | B2 | 11/2018 | During |
| 2001/0024659 | A1 | 9/2001 | Chen et al. |
| 2006/0147947 | A1 | 7/2006 | Apfeld |
| 2008/0188457 | A1 | 8/2008 | Barlow et al. |
| 2008/0220092 | A1 | 9/2008 | Dipierro et al. |
| 2016/0193231 | A1 | 7/2016 | Scheer et al. |

FOREIGN PATENT DOCUMENTS

CA       2494281 A1    2/2004

OTHER PUBLICATIONS

Zhu et al., Cancer Prev Res, Jun. 2015;8(6):518-27.

Johnson, "Metformin Use in Women with Polycystic Ovary Syndrome", Annals of Translational Medicine; 2014, vol. 2, No. 6 (56);7 pages.
Buse et al., "The Primary Glucose-Lowering Effect of Metformin Resides in the Gut, Not the Circulation. Results From Short-term Pharmacokinetic and 12-Week Dose-Ranging Studies," Diabetes Care, Aug. 18, 2015; pp. 1-8.
Yang et al., "Phenotypes of Hypofrontality in Older Female Fragile X Premutation Carriers," Ann Neurol., Aug. 2013, vol. 74, No. 2; pp. 275-283.
Yang et al., "Neural Substrates of Executive Dysfunction in Fragile X-Associated Tremor/Ataxia Syndrome (FXTAS): a Brain Potential Study," Cerebral Cortex; Nov. 2013, vol. 23; pp. 2657-2666.
Krogsgaard-Larsen et al., "Deuterium Labelling of the GABA Agonists Thip, Piperidine-4-Sulphonic Acid and The GABA Uptake Inhibitor THPO," Journal of Labelled Compounds and Radiopharmaceuticals, vol. XIX, No. 5; pp. 389-702.
Kasznicki, et al., "Metformin in Cancer Prevention and Therapy," Annals of Translational Medicine, 2014, vol. 2, No. 6 (57); 11 pages.
Pernicova et al., "Metformin—Mode of Action and Clinical Implications for Diabetes and Cancer," Nature Reviews—Endocrinology, vol. 10, Mar. 2014; pp. 143-156.
Hagerman et al., "Treatment of Fragile X-associated Tremor Ataxia Syndrome (FXTAS) and Related Neurological Problems," Clinical Interventions in Aging, 2008, vol. 3, No. 2, pp. 251-262.
Gong et al., Metformin Pathways: Pharmacokinetics and Pharmacodynamics, Pharmacogenet Genomics, Nov. 2012, vol. 22, No. 11; pp. 820-827.
International Search Report and Written Opniion, dated Jan. 12, 2018, corresponding to counterpart International Application No. PCT/US17/47505; 15 total pages.
Allard et al., "Prolonged metformin treatment leads to reduced transcription of Nrf2 and neurotrophic factors without cognitive impairment in older C57BL/6J mice", Behav Brain Res., Author manuscript; vol. 301: 1-9; Mar. 15, 2016 (22 pages).
Hsu et al., "Incidence of Dementia is Increased in Type 2 Diabetes and Reduced by the Use of Sulfonylureas and Metformin", Journal of Alzheimer's Disease (2011), vol. 24, Dec. 13, 2010; pp. 485-493.
Ryan et al., "Improving Metabolic Control Leads to Better Working Memory in Adults With Type 2 Diabetes", Diabetes Care, vol. 29, No. 2, Feb. 2006, pp. 345-351.

*Primary Examiner* — San Ming R Hui
(74) *Attorney, Agent, or Firm* — Carter, DeLuca & Farrell LLP

(57) ABSTRACT

Methods of treating developmental disorders such as Angelman syndrome, Fragile X syndrome, Fragile X-associated tremor/ataxia syndrome (FXTAS), Autistic Spectrum Disorder, Autism, Asperger's syndrome, pervasive developmental disorder, Childhood Disintegrative Disorder, Rett syndrome, Landau-Kleffner Syndrome, Prader-Willi Syndrome, Tardive Dyskinesia, a seizure disorder and/or Williams Syndrome with a biguanide such as metformin, buformin, phenformin or a pharmaceutically acceptable salt thereof are provided. The methods provide therapeutic compositions that may be used to improve one or more symptoms of the developmental disorder.

21 Claims, No Drawings

METHODS OF TREATING DEVELOPMENTAL DISORDERS WITH BIGUANIDES

CROSS REFERENCE TO RELATED APPLICATIONS

This application is a continuation application of U.S. patent application Ser. No. 15/680,417, filed on Aug. 18, 2017, which claims benefit of and priority to U.S. Provisional Application No. 62/376,488, filed Aug. 18, 2016, which are incorporated herein by reference in their entireties.

TECHNICAL FIELD

Methods of treating developmental disorders with biguanides are provided.

BACKGROUND

Biguanides such as metformin, buformin and phenformin have been used as antihyperglycemic agents in the treatment of diabetes. Metformin decreases hepatic glucose production, decreases intestinal absorption of glucose, and improves insulin sensitivity by increasing peripheral glucose uptake and utilization. The mechanistic aspects of metformin action are unclear. See, Pernicova and Korbonits, *Nature Reviews Endocrinol.*, 2014;10:143-156. Metformin has also been used in the treatment of polycystic ovary syndrome (PCOS) and anovulatory infertility in women with PCOS. See, e.g., Johnson, *Ann. Transl. Med.*, 2014, 2(6):56. Metformin is being investigated for cancer prevention and therapy. See, e.g., Kasznicki et al., *Ann. Transl. Med.*, 2014; 2(6):57. The anticancer molecular action of metformin has been associated with the inhibition of the mammalian target of rapamycin complex 1 (mTORC1). Id. The mTOR pathway plays a pivotal role in metabolism, growth and proliferation of cancer cells. Id. Metformin is believed to inhibit mTORC1 pathway. Id.

Treatments for developmental disorders such as Autistic Spectrum Disorder, Rett syndrome, Angelman syndrome, Fragile X syndrome, and Fragile X-associated tremor/ataxia syndrome are limited. Angelman syndrome is a neurodevelopmental disorder caused by loss of function of the UBE3A gene encoding a ubiquitin E3 ligase. Motor dysfunction is a characteristic feature of Angelman syndrome, but neither the mechanisms of action nor effective therapeutic strategies have yet been elucidated.

Fragile X syndrome may be the most common genetic cause of intellectual disability and the most common single-gene cause of autism. It is caused by mutations on the fragile X mental retardation gene (FMR1) and lack of fragile X mental retardation protein, which in turn, leads to decreased inhibition of translation of many synaptic proteins. The main efforts have focused on metabotropic glutamate receptor (mGluR) targeted treatments; however, investigation on the gamma-aminobutyric acid (GABA) system and its potential as a targeted treatment is less emphasized. The fragile X mouse models (Fmr1-knock out) show decreased GABA subunit receptors, decreased synthesis of GABA, increased catabolism of GABA, and overall decreased GABAergic input in many regions of the brain. These symptoms are also observed in individuals with autism and other neurodevelopmental disorders, therefore the targeted treatments for Fragile X syndrome are leading the way in the treatment of other neurodevelopmental syndromes and autism. Potential GABAergic treatments, such as riluzole, gaboxadol, tiagabine, and vigabatrin have been discussed. However, further studies are needed to determine the safety and efficacy of GABAergic treatments for Fragile X syndrome.

Fragile X-associated tremor/ataxia syndrome (FXTAS) is a late-onset disorder, usually occurring after age 50. Mutations in the FMR1 gene increase the risk of developing FXTAS. The mutation relates to a DNA segment known as a CGG triplet repeat which is expanded within the FMR1 gene. Normally, this DNA segment is repeated from 5 to about 40 times. In people with FXTAS the CGG segment may be repeated 55 to 200 times. This mutation is known as an FMR1 gene premutation. An expansion of more than 200 repeats, a full mutation, causes Fragile X syndrome discussed above. FXTAS is typically characterized by problems with movement and thinking ability (cognition). FXTAS signs and symptoms usually worsen with age. Affected individuals have areas of damage in the cerebellum, the area of the brain that controls movement. Characteristic features of FXTAS are intention tremor, which is trembling or shaking of a limb when trying to perform a voluntary movement such as reaching for an object, and problems with coordination and balance (ataxia). Many affected individuals develop other movement problems, such as parkinsonism, which includes tremors when not moving (resting tremor), rigidity, and unusually slow movement (bradykinesia). In addition, affected individuals may have reduced sensation, numbness or tingling, pain, or muscle weakness in the lower limbs, and inability to control the bladder or bowel. Other symptoms may include chronic pain syndromes, such as fibromyalgia and chronic migraine, hypothyroidism, hypertension, insomnia, sleep apnea, vertigo, olfactory dysfunction, and hearing loss. People with FXTAS commonly have cognitive disabilities such as short-term memory loss and loss of executive function, which is the ability to plan and implement actions and develop problem-solving strategies. Loss of this function impairs skills such as impulse control, self-monitoring, focusing attention appropriately, and cognitive flexibility. Many people with FXTAS experience psychiatric symptoms such as anxiety, depression, moodiness, or irritability.

There is currently no targeted therapeutic intervention that can arrest or reverse the pathogenesis of FXTAS. However a number of treatment approaches of potential symptomatic benefit have been suggested. Primidone, beta-blockers such as propanolol, topiramate, carbidopa/levodopa, and benzodiazepines have been suggested to control tremors associated with FXTAS; botulinum toxin for involuntary muscle activities, such as dystonia and spasticity; carbidopa/levodopa, amantadine and buspirone for ataxia; cholinesterase inhibitors such as donepezil, and memantine (an NMDA antagonist) for cognitive deficits and dementia; and antidepressants and antipsychotics for psychiatric symptoms. See, e.g., Hagerman, et al., Clin Intery Aging. 2008 Jun; 3(2): 251-262.

Rett syndrome is a neurodevelopmenal disorder that typically affects girls. It is characterized by normal early growth and development followed by a slowing of development, loss of purposeful use of the hands, distinctive hand movements, slowed brain and head growth, problems with walking, seizures, and intellectual disability. Nearly all cases of Rett syndrome are caused by a mutation in the methyl CpG binding protein 2, or MECP2 gene. The MECP2 gene contains instructions for the synthesis of methyl cytosine binding protein 2 (MeCP2), which is utilized in brain development and acts as one of the many biochemical switches that can either increase or decrease gene expression. The main diagnostic criteria or symptoms include partial or complete loss of acquired purposeful hand skills, partial or complete loss of acquired spoken language, repetitive hand movements (such has hand wringing or squeezing, clapping or rubbing), and gait abnormalities, including toe-walking or an unsteady, wide-based, stiff-legged walk. Supportive criteria are not required for a diagnosis of Rett syndrome but may occur in some individuals. In addition, these symptoms, which vary in severity from child to child, may not be observed in very young children but may develop with age. A child with supportive criteria but none of the essential criteria does not have Rett syndrome. Supportive criteria include scoliosis, teeth-grinding, small cold hands and feet in relation to height, abnormal sleep patterns, abnormal muscle tone, heart abnormalities, inappropriate laughing or screaming, intense eye communication, and diminished response to pain.

There is no cure for Rett syndrome. Treatment for the disorder is symptomatic, focusing on the management of symptoms, and supportive, requiring a multidisciplinary approach. Medication may be needed for breathing irregularities and motor difficulties, and anticonvulsant drugs may be used to control seizures.

Accordingly, there remains a need for effective treatments of patients with developmental disorders, such as Autistic Spectrum Disorder, pervasive developmental disorder, Autism, Angelman syndrome, Fragile X syndrome, Fragile X-associated tremor/ataxia syndrome (FXTAS), Rett syndrome, Asperger's syndrome, Childhood Disintegrative Disorder, Attention-deficit/hyperactivity disorder (ADHD), Prader-Willi Syndrome, Landau-Kleffner Syndrome, Rasmussen's syndrome, Dravet syndrome, Tardive Dyskinesia, Williams Syndrome and/or seizure disorders such as Doose syndrome, CDKL5 disorder, West's syndrome, Lennox-Gastaut syndrome (LGS) and Ohtahara syndrome.

SUMMARY

Methods of treating a developmental disorder described herein include administering a biguanide or a pharmaceutically acceptable salt thereof to a patient in need thereof to provide improvement in one or more symptoms of the disorder. In embodiments, methods of treating a developmental disorder described herein include administering metformin or a pharmaceutically acceptable salt thereof to a patient in need thereof to provide improvement in one or more symptoms of the disorder. In embodiments, methods of treating a developmental disorder described herein include administering a biguanide or a pharmaceutically acceptable salt thereof to a patient in need thereof to provide improvement in next day functioning of the patient. In embodiments, methods of treating a developmental disorder described herein include administering metformin or a pharmaceutically acceptable salt thereof to a patient in need thereof to provide improvement in next day functioning of the patient. In embodiments, methods of treating a developmental disorder described herein include administering buphormin or a pharmaceutically acceptable salt thereof to a patient in need thereof to provide improvement in one or more symptoms of the disorder. In embodiments, methods of treating a developmental disorder described herein include administering phenformin or a pharmaceutically acceptable salt thereof to a patient in need thereof to provide improvement in one or more symptoms of the disorder. In embodiments, methods of treating a developmental disorder described herein include administering buphormin or a pharmaceutically acceptable salt thereof to a patient in need thereof to provide improvement in next day functioning of the patient. In embodiments, methods of treating a developmental disorder described herein include administering phenformin or a pharmaceutically acceptable salt thereof to a patient in need thereof to provide improvement next day functioning of the patient.

In embodiments, the developmental disorder may be an Autistic Spectrum Disorder, pervasive developmental disorder, Autism, Angelman syndrome, Fragile X syndrome, Fragile X-associated tremor/ataxia syndrome (FXTAS), Rett syndrome, Asperger's syndrome, Childhood Disintegrative Disorder, Attention-deficit/hyperactivity disorder (ADHD), Landau-Kleffner Syndrome, Prader-Willi Syndrome, Rasmussen's syndrome, Dravet syndrome, Tardive Dyskinesia, seizure disorder and/or Williams Syndrome. In embodiments, the developmental disorder may be a seizure disorder such as epilepsy, epilepsy with generalized tonic-clonic seizures, epilepsy with myoclonic absences, frontal lobe epilepsy, temporal lobe epilepsy, infantile spasms (West syndrome), childhood absence epilepsy, juvenile myoclonic epilepsy (JME), vaccine-related encephalopathy, intractable childhood epilepsy (ICE), essential tremor, acute repetitive seizures, benign rolandic epilepsy, status epilepticus, refractory status, epilepticus, super-refractory status epilepticus (SRSE), PCDH19 pediatric epilepsy, increased seizure activity (also called serial or cluster seizures), or breakthrough seizures. In embodiments, the developmental disorder may be a seizure disorder such as Doose syndrome, CDKL5 disorder, West's syndrome, Lennox-Gastaut syndrome (LGS) and Ohtahara syndrome. In embodiments, the seizure disorder is associated with a sodium channel protein type 1 subunit alpha (Scn1a)-related disorder. In embodiments, the seizure disorder may either be associated with, or independent of, any of the above-listed developmental disorders.

DETAILED DESCRIPTION

Described herein are methods of treating developmental disorders with a biguanide or a pharmaceutically acceptable salt thereof. Many pharmaceutical products are administered as a fixed dose, at regular intervals, to achieve therapeutic efficacy. Its duration of action may be reflected by its plasma half-life. Metformin has a plasma elimination half-life (t½) reportedly between 1.5 hours and 6.2 hours. See, e.g., Gong, et al., Pharmacogenet Genomics. 2012 Nov; 22(11): 820-827 (5 hours). Buformin has a t½ reported to be 4 hours. Phenformin has a t½ reported to be 10 to 15 hours. Since efficacy is often dependent on sufficient exposure within the central nervous system administration of CNS drugs with a short half-life may require frequent maintenance dosing.

Advantageously disclosed herein are methods of treating developmental disorders by administration of biguanides such as metformin, buformin and pheformin or a pharmaceutically acceptable salt thereof. For example, in embodiments, methods of treating a developmental disorder are provided which include administering to a patient in need thereof about 50 mg to about 3000 mg metformin or a pharmaceutically acceptable salt thereof wherein the patient exhibits improvement in one or more symptoms of the disorder. In embodiments, methods of treating a developmental disorder are provided which include administering to a patient in need thereof about 50 mg to about 3000 mg metformin or a pharmaceutically acceptable salt thereof wherein the patient exhibits improvement in one or more symptoms of the disorder for more than 6 hours after administration to the patient. In embodiments, methods of treating a developmental disorder are provided which include administering to a patient in need thereof about 50 mg to about 3000 mg metformin or a pharmaceutically acceptable salt thereof wherein the patient exhibits improvement in one or more symptoms of the disorder for more than 12 hours after administration to the patient.

In embodiments, methods of treating a developmental disorder are provided which include administering to a patient in need thereof a pharmaceutical composition including about 50 mg to about 3000 mg metformin or a pharmaceutically acceptable salt thereof wherein the composition provides improvement in one or more symptoms of the disorder. In embodiments, methods of treating a developmental disorder are provided which include administering to a patient in need thereof a pharmaceutical composition including about 50 mg to about 3000 mg metformin or a pharmaceutically acceptable salt thereof wherein the composition provides improvement in one or more symptoms of the disorder for more than 6 hours after administration to the patient. In embodiments, methods of treating a developmental disorder are provided which include administering to a patient in need thereof a pharmaceutical composition including about 50 mg to about 3000 mg metformin or a pharmaceutically acceptable salt thereof wherein the composition provides improvement in one or more symptoms of the disorder for more than 12 hours after administration to the patient.

In embodiments, the developmental disorder is an Autistic Spectrum Disorder (ASD), pervasive developmental disorder, autism, Angelman syndrome, Fragile X syndrome, Fragile X-associated tremor/ataxia syndrome (FXTAS), Rett syndrome, Asperger's syndrome, Childhood Disintegrative Disorder, Attention-deficit/hyperactivity disorder (ADHD), Lennox-Gastaut syndrome (LGS), Landau-Kleffner Syndrome, Prader-Willi Syndrome, Ohtahara syndrome, Rasmussen's syndrome, Dravet syndrome, Doose syndrome, CDKL5 disorder, Tardive Dyskinesia, and/or Williams Syndrome, and/or Williams Syndrome. In embodiments, the developmental disorder is Autism, Rett syndrome, Angelman syndrome, and/or Fragile X syndrome. In embodiments, the developmental disorder is a pervasive developmental disorder not otherwise characterized (PDD-NOS). Symptoms of PDD-NOS can vary widely from one child to the next. Overall, child with PDD-NOS can be characterized as having impaired social interaction, better language skills than children with autistic disorder but not as good as those with Asperger's syndrome, fewer repetitive behaviors than children with Asperger's syndrome or autistic disorder, and a later age of onset.

In embodiments, the developmental disorder is autism. In embodiments, the developmental disorder is Angelman syndrome. In embodiments the development disorder is Fragile X syndrome. In embodiments, the developmental disorder is Fragile X-associated tremor/ataxia syndrome (FXTAS). In embodiments, the developmental disorder is Rett syndrome.

In embodiments, the developmental disorder is a seizure disorder such as epilepsy, epilepsy with generalized tonic-clonic seizures, epilepsy with myoclonic absences, frontal lobe epilepsy, temporal lobe epilepsy, infantile spasms (West syndrome), childhood absence epilepsy, juvenile myoclonic epilepsy (JME), vaccine-related encephalopathy, intractable childhood epilepsy (ICE), essential tremor, acute repetitive seizures, benign rolandic epilepsy, status epilepticus, refractory status, epilepticus, super-refractory status epilepticus (SRSE), PCDH19 pediatric epilepsy, increased seizure activity (also called serial or cluster seizures), or breakthrough seizures. In embodiments, the seizure disorder is Doose syndrome, CDKL5 disorder, West's syndrome, Lennox-Gastaut syndrome (LGS) and Ohtahara syndrome. In embodiments, the seizure disorder is associated with a sodium channel protein type 1 subunit alpha (Scn1a)-related disorder. In embodiments, the seizure disorder may either be associated with, or independent of, any of the above-listed developmental disorders.

Embodiments described herein provide that a patient in need thereof is administered a pharmaceutical composition including a biguanide or a pharmaceutically acceptable salt thereof. Biguanides may be provided as an acid addition salt. For example, metformin, buformin and phenformin acid addition salts, include but are not limited to, hydrochloric, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, sulfuric, sulfamic, phosphoric or nitric acid addition salts may be used. Fatty acid salts may be used, e.g., laureate, succinate, caprate, palmitate, etc. Hydroxyacid salts may be used, including salts of hydroxy-aliphatic dicarboxylic acids, such as mesotartaric acid, tartaric acid, mesoxalic acids and oxidised maleates. Other salts may include pamoate, p-chlorophenoxyacetic, acetylsalicylic, nicotinic, and the like.

Deuteration of pharmaceuticals to improve pharmacokinetics (PK), pharmacodynamics (PD), and toxicity profiles, has been demonstrated previously with some classes of drugs. Accordingly the use of deuterium enriched biguanides is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art to provide deuterium enriched metformin. See Journal of Labeled Compounds and Radiopharmaceuticals 19(5) 689-702 (1982).

Deuterium enriched biguanides may be described by the percentage of incorporation of deuterium at a given position in the molecule in the place of hydrogen. For example, deuterium enrichment of 1% at a given position means that 1% of molecules in a given sample contain deuterium at that specified position. The deuterium enrichment can be determined using conventional analytical methods, such as mass spectrometry and nuclear magnetic resonance spectroscopy. In embodiments deuterium enriched biguanides means that the specified position is enriched with deuterium above the naturally occurring distribution (i.e., above about 0.0156%). In embodiments, deuterium enrichment is no less than about 1%, no less than about 5%, no less than about 10%, no less than about 20%, no less than about 50%, no less than about 70%, no less than about 80%, no less than about 90%, or no less than about 98% of deuterium at a specified position.

In embodiments, methods of treating a developmental disorder include administering to a patient in need thereof about 50 mg to about 3000 mg metformin or a pharmaceutically acceptable salt thereof. In embodiments, about 50 mg to about 3000 mg of metformin or a pharmaceutically acceptable salt thereof is administered in 24 hours. In embodiments, the metformin or a pharmaceutically acceptable salt thereof is administered in divided doses over 24 hours.

In embodiments, the patient is administered 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg, to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, 725 mg to 750 mg, 750 mg to 775 mg, 775 mg to 800 mg, 800 mg to 825 mg, 825 mg to 850 mg, 850 mg to 875 mg, 875 mg to 900 mg, 900 mg to 925 mg, 925 mg to 950 mg, 950 mg to 975 mg, 975 mg to 1000 mg, 1000 mg to 1025 mg, 1025 mg to 1050 mg, 1050 mg to 1075 mg, 1075 mg to 1100 mg, 1100 mg to 1125 mg, 1125 mg to 1150 mg, 1150 mg to 1175 mg, 1175 mg to 1200 mg, 1200 mg to 1225 mg, 1225 mg to 1250 mg, 1250 mg to 1275 mg, 1275 mg to 1300 mg, 1300 mg to 1325 mg, 1325 mg to 1350 mg, 1350 mg to 1375 mg, 1375 mg to 1400 mg, 1400 mg to 1425 mg, 1425 mg to 1450 mg, 1450 mg to 1475 mg, 1475 mg to 1500 mg, 1500 mg to 1525 mg, 1525 mg to 1550 mg, 1550 mg to 1575 mg, 1575 mg to 1600 mg, 1600 mg to 1625 mg, 1625 mg to 1650 mg, 1650 mg to 1675 mg, 1675 mg to 1700 mg, 1700 mg to 1725 mg, 1725 mg to 1750 mg, 1750 mg to 1775 mg, 1775 mg to 1800 mg, 1800 mg to 1825 mg, 1825 mg to 1850 mg, 1850 mg to 1875 mg, 1875 mg to 1900 mg, 1900 mg to 1925 mg, 1925 mg to 1950 mg, 1950 mg to 1975 mg, 1975 mg to 2000 mg, 2000 mg to 2025 mg, 2025 mg to 2050 mg, 2050 mg to 2075 mg, 2075 mg to 2100 mg, 2100 mg to 2125 mg, 2125 mg to 2150 mg, 2150 mg to 2175 mg, 2175 mg to 2200 mg, 2200 mg to 2225 mg, 2225 mg to 2250 mg, 2250 mg to 2275 mg, 2275 mg to 2300 mg, 2300 mg to 2325 mg, 2325 mg to 2350 mg, 2350 mg to 2375 mg, 2375 mg to 2400 mg, 2400 mg to 2425 mg, 2425 mg to 2450 mg, 2450 mg to 2475 mg, 2475 mg to 2500 mg, 2500 mg to 2525 mg, 2525 mg to 2550 mg, 2550 mg to 2575 mg, 2575 mg to 2600 mg, 2600 mg to 2625 mg, 2625 mg to 2650 mg, 2650 mg to 2675 mg, 2675 mg to 2700 mg, 2700 mg to 2725 mg, 2725 mg to 2750 mg, 2750 mg to 2775 mg, 2775 mg to 2800 mg, 2800 mg to 2825 mg, 2825 mg to 2850 mg, 2850 mg to 2875 mg, 2875 mg to 2900 mg, 2900 mg to 2925 mg, 2925 mg to 2950 mg, 2950 mg to 2975 mg, or 2975 mg to 3000 mg, metformin or a pharmaceutically acceptable salt thereof.

In embodiments, the patient is administered 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1225 mg, 1250 mg, 1275 mg, 1300 mg, 1325 mg, 1350 mg, 1375 mg, 1400 mg, 1425 mg, 1450 mg, 1475 mg, 1500 mg, 1525 mg, 1550 mg, 1575 mg, 1600 mg, 1625 mg, 1650 mg, 1675 mg, 1700 mg, 1725 mg, 1750 mg, 1775 mg, 1800 mg, 1825 mg, 1850 mg, 1875 mg, 1900 mg, 1925 mg, 1950 mg, 1975 mg, 2000 mg, 2025 mg, 2250 mg, 2275 mg, 2300 mg, 2325 mg, 2350 mg, 2375 mg, 2400 mg, 2425 mg, 2450 mg, 2475 mg, 2500 mg, 2525 mg, 2550 mg, 2575 mg, 2600 mg, 2625 mg, 2650 mg, 2675 mg, 2700 mg, 2725 mg, 2750 mg, 2775 mg, 2800 mg, 2825 mg, 2850 mg, 2875 mg, 2900 mg, 2925 mg, 2950 mg, 2975 mg, or 3000 mg, metformin or a pharmaceutically acceptable salt thereof.

In embodiments methods of treating a developmental disorder include administering to a patient in need thereof a pharmaceutical composition including about 50 mg to about 3000 mg metformin or a pharmaceutically acceptable salt thereof.

In embodiments, the pharmaceutical compositions include 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 500 mg to 525 mg, 525 mg to 550 mg, 550 mg to 575 mg, 575 mg to 600 mg, 600 mg to 625 mg, 625 mg to 650 mg, 650 mg to 675 mg, 675 mg to 700 mg, 700 mg to 725 mg, 725 mg to 750 mg, 750 mg to 775 mg, 775 mg to 800 mg, 800 mg to 825 mg, 825 mg to 850 mg, 850 mg to 875 mg, 875 mg to 900 mg, 900 mg to 925 mg, 925 mg to 950 mg, 950 mg to 975 mg, 975 mg to 1000 mg, 1000 mg to 1025 mg, 1025 mg to 1050 mg, 1050 mg to 1075 mg, 1075 mg to 1100 mg, 1100 mg to 1125 mg, 1125 mg to 1150 mg, 1150 mg to 1175 mg, 1175 mg to 1200 mg, 1200 mg to 1225 mg, 1225 mg to 1250 mg, 1250 mg to 1275 mg, 1275 mg to 1300 mg, 1300 mg to 1325 mg, 1325 mg to 1350 mg, 1350 mg to 1375 mg, 1375 mg to 1400 mg, 1400 mg to 1425 mg, 1425 mg to 1450 mg, 1450 mg to 1475 mg, 1475 mg to 1500 mg, 1500 mg to 1525 mg, 1525 mg to 1550 mg, 1550 mg to 1575 mg, 1575 mg to 1600 mg, 1600 mg to 1625 mg, 1625 mg to 1650 mg, 1650 mg to 1675 mg, 1675 mg to 1700 mg, 1700 mg to 1725 mg, 1725 mg to 1750 mg, 1750 mg to 1775 mg, 1775 mg to 1800 mg, 1800 mg to 1825 mg, 1825 mg to 1850 mg, 1850 mg to 1875 mg, 1875 mg to 1900 mg, 1900 mg to 1925 mg, 1925 mg to 1950 mg, 1950 mg to 1975 mg, 1975 mg to 2000 mg, 2000 mg to 2025 mg, 2025 mg to 2050 mg, 2050 mg to 2075 mg, 2075 mg to 2100 mg, 2100 mg to 2125 mg, 2125 mg to 2150 mg, 2150 mg to 2175 mg, 2175 mg to 2200 mg, 2200 mg to 2225 mg, 2225 mg to 2250 mg, 2250 mg to 2275 mg, 2275 mg to 2300 mg, 2300 mg to 2325 mg, 2325 mg to 2350 mg, 2350 mg to 2375 mg, 2375 mg to 2400 mg, 2400 mg to 2425 mg, 2425 mg to 2450 mg, 2450 mg to 2475 mg, 2475 mg to 2500 mg, 2500 mg to 2525 mg, 2525 mg to 2550 mg, 2550 mg to 2575 mg, 2575 mg to 2600 mg, 2600 mg to 2625 mg, 2625 mg to 2650 mg, 2650 mg to 2675 mg, 2675 mg to 2700 mg, 2700 mg to 2725 mg, 2725 mg to 2750 mg, 2750 mg to 2775 mg, 2775 mg to 2800 mg, 2800 mg to 2825 mg, 2825 mg to 2850 mg, 2850 mg to 2875 mg, 2875 mg to 2900 mg, 2900 mg to 2925 mg, 2925 mg to 2950 mg, 2950 mg to 2975 mg, 2975 mg to 3000 mg, metformin or a pharmaceutically acceptable salt thereof.

In embodiments, the pharmaceutical compositions include 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1225 mg, 1250 mg, 1275 mg, 1300 mg, 1325 mg, 1350 mg, 1375 mg, 1400 mg, 1425 mg, 1450 mg, 1475 mg, 1500 mg, 1525 mg, 1550 mg, 1575 mg, 1600 mg, 1625 mg, 1650 mg, 1675 mg, 1700 mg, 1725 mg, 1750 mg, 1775 mg, 1800 mg, 1825 mg, 1850 mg, 1875 mg, 1900 mg, 1925 mg, 1950 mg, 1975 mg, 2000 mg, 2025 mg, 2250 mg, 2275 mg, 2300 mg, 2325 mg, 2350 mg, 2375 mg, 2400 mg, 2425 mg, 2450 mg, 2475 mg, 2500 mg, 2525 mg, 2550 mg, 2575 mg, 2600 mg, 2625 mg, 2650 mg, 2675 mg, 2700 mg, 2725 mg, 2750 mg, 2775 mg, 2800 mg, 2825 mg, 2850 mg, 2875 mg, 2900 mg, 2925 mg, 2950 mg, 2975 mg, 3000 mg, metformin or a pharmaceutically acceptable salt thereof.

In embodiments, methods of treating a developmental disorder include administering to a patient in need thereof about 10 mg to about 500 mg buformin or a pharmaceutically acceptable salt thereof In embodiments, the amount of buformin or a pharmaceutically acceptable salt thereof is administered in 24 hours. In embodiments, the buformin or a pharmaceutically acceptable salt thereof is administered in divided doses over 24 hours.

In embodiments, the patient is administered 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, or 475 mg to 500 mg, buformin or a pharmaceutically acceptable salt thereof.

In embodiments, the patient is administered 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, 300 mg, 325 mg, 350 mg, 375 mg, 400 mg, 425 mg, 450 mg, 475 mg, or 500 mg, buformin or a pharmaceutically acceptable salt thereof.

In embodiments methods of treating a developmental disorder include administering to a patient in need thereof a pharmaceutical composition including about 10 mg to about 500 mg buformin or a pharmaceutically acceptable salt thereof.

In embodiments, the compositions include 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, or 475 mg to 500 mg, buformin or a pharmaceutically acceptable salt thereof.

In embodiments, the compositions include 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, 300 mg, 325 mg, 350 mg, 375 mg, 400 mg, 425 mg, 450 mg, 475 mg, or 500 mg, buformin or a pharmaceutically acceptable salt thereof.

In embodiments, methods of treating a developmental disorder include administering to a patient in need thereof about 10 mg to about 300 mg phenformin or a pharmaceutically acceptable salt thereof In embodiments, the amount of phenformin or a pharmaceutically acceptable salt thereof is administered in 24 hours. In embodiments, the phenformin or a pharmaceutically acceptable salt thereof is administered in divided doses over 24 hours.

In embodiments, the patient is administered 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, or 275 mg to 300 mg, phenformin or a pharmaceutically acceptable salt thereof.

In embodiments, the patient is administered 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, or 300 mg, phenformin or a pharmaceutically acceptable salt thereof.

In embodiments methods of treating a developmental disorder include administering to a patient in need thereof a pharmaceutical composition including about 10 mg to about 300 mg phenformin or a pharmaceutically acceptable salt thereof.

In embodiments, the compositions include 10 mg to 15 mg, 15 mg to 20 mg, 20 mg to 25 mg, 25 mg to 30 mg, 30 mg to 35 mg, 35 mg to 40 mg, 40 mg to 45 mg, 45 mg to 50 mg, 50 mg to 55 mg, 55 mg to 60 mg, 60 mg to 75 mg, 75 mg, to 80 mg, 80 mg to 85 mg, 85 mg to 90 mg, 90 mg to 95 mg, 95 mg to 100 mg, 100 mg to 110 mg, 110 mg to 115 mg, 115 mg to 120 mg, 125 mg to 130 mg, 130 mg to 135 mg, 135 mg to 140 mg, 140 mg to 145 mg, 145 mg to 150 mg, 150 mg to 155 mg, 155 mg to 160 mg, 160 mg, to 165 mg, 165 mg to 170 mg, 175 mg to 180 mg, 180 mg to 185 mg, 185 mg to 190 mg, 190 mg to 195 mg, 195 to 200 mg, 200 mg to 225 mg, 225 mg to 250 mg, 250 mg to 275 mg, or 275 mg to 300 mg, phenformin or a pharmaceutically acceptable salt thereof.

In embodiments, the compositions include 10 mg, 15 mg, 20 mg, 25 mg, 30 mg, 35 mg, 40 mg, 45 mg, 50 mg, 55 mg, 60 mg, 75 mg, 80 mg, 85 mg, 90 mg, 95 mg, 100 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg, 275 mg, or 300 mg, phenformin or a pharmaceutically acceptable salt thereof.

Pharmaceutical compositions herein may be provided with immediate release, delayed release, extended release, or modified release profiles. In embodiments, pharmaceutical compositions with different drug release profiles may be combined to create a two phase or three-phase release profile. For example, pharmaceutical compositions may be provided with an immediate release and an extended release profile. In embodiments, pharmaceutical compositions may be provided with an extended release and delayed release profile. Such composition may be provided as pulsatile formulations, multilayer tablets, or capsules containing tablets, beads, granules, etc. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions.

In embodiments, the pharmaceutical compositions described herein may be administered once, twice, or three times daily, four times daily or every other day. In embodiments, a pharmaceutical composition described herein is provided to the patient in the morning. In embodiments, a pharmaceutical composition described herein is provided to the patient in the evening. In embodiments, a pharmaceutical composition described herein is provided to the patient once in the evening and once in the morning. In embodiments, the total amount of metformin or a pharmaceutically acceptable salt thereof administered to a subject in a 24-hour period is 50 mg to 3000 mg. In embodiments, the total amount of metformin or a pharmaceutically acceptable salt thereof administered to a subject in a 24-hour period is 100 mg to 2550 mg. In embodiments, the total amount of metformin or a pharmaceutically acceptable salt thereof administered to a subject in a 24-hour period is 500 mg, 600 mg, 750 mg, 800 mg, 850 mg, 1000 mg, 1200 mg, 1600 mg, 2000 mg or 2550 mg. In embodiments, the total amount of metformin or a pharmaceutically acceptable salt thereof administered to a subject in a 24-hour period is 1500 mg.

In embodiments, provided herein are methods of treating a developmental disorder including administering to a patient in need thereof a pharmaceutical composition including a biguanide such as metformin, buformin, phenformin, or a pharmaceutically acceptable salt thereof wherein the patient exhibits improvement in at least one symptom of the developmental disorder. Symptoms may include, but are not limited to, ataxia, gait, speech impairment, vocalization, cognition, motor activity, clinical seizure, subclinical seizure, hypotonia, hypertonia, feeding difficulty, drooling, mouthing behavior, sleep difficulties, hand flapping, hand ringing, teeth grinding, easily provoked laughter and short attention span. In embodiments, provided in accordance with the present disclosure is improvement in cognition. Cognition refers to the mental processes involved in gaining knowledge and comprehension, such as thinking, knowing, remembering, judging, and problem solving. These higher-level functions of the brain encompass language, imagination, perception, and the planning and execution of complex behaviors.

In embodiments, provided herein are methods of treating a developmental disorder including administering to a patient in need thereof a pharmaceutical composition including a biguanide such as metformin, buformin, phenformin, or a pharmaceutically acceptable salt thereof, wherein the composition provides improvement of at least one symptom for more than 4 hours after administration of the pharmaceutical composition to the patient. In embodiments, the improvement of at least one symptom for more than 6 hours after administration of the pharmaceutical composition to the patient is provided in accordance with the present disclosure. In embodiments, improvement of at least one symptom for more than, e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one symptom for at least e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one symptom for 12 hours after administration of the pharmaceutical composition to the patient is provided in accordance with the present disclosure.

In embodiments, provided herein are methods of treating a developmental disorder including administering to a patient in need thereof a pharmaceutical composition including a biguanide such as metformin, buformin, phenformin, or a pharmaceutically acceptable salt thereof wherein the composition provides improvement in next day functioning to the patient.

In embodiments, provided herein are methods of treating a developmental disorder including administering to a patient in need thereof a biguanide such as metformin, buformin, phenformin, or a pharmaceutically acceptable salt thereof which provides an in vivo plasma profile, wherein the in vivo plasma profile of the patient 10 hours after administration of the biguanide or a pharmaceutically acceptable salt thereof is reduced by more than 50% and the method provides improvement in the patient for more than 10, 12, 14, 16, 18, 20, 22 or 24 hours after administration. In embodiments, provided herein are methods of treating a developmental disorder including administering to a patient in need thereof the biguanide or a pharmaceutically acceptable salt thereof which provides an in vivo plasma profile, wherein the in vivo plasma profile of the patient 10 hours after administration of the biguanide or a pharmaceutically acceptable salt thereof is reduced by more than 55% and the method provides improvement in the patient for more than 10, 12, 14, 16, 18, 20, 22 or 24 hours after administration. In embodiments, provided herein are methods of treating a developmental disorder including administering to a patient in need thereof the biguanide or a pharmaceutically acceptable salt thereof which provides an in vivo plasma profile, wherein the in vivo plasma profile of the patient 10 hours after administration of the biguanide or a pharmaceutically acceptable salt thereof is reduced by more than 60% and the method provides improvement in the patient for more than 10, 12, 14, 16, 18, 20, 22 or 24 hours after administration. In embodiments, provided herein are methods of treating a developmental disorder including administering to a patient in need thereof the biguanide or a pharmaceutically acceptable salt thereof which provides an in vivo plasma profile, wherein the in vivo plasma profile of the patient 10 hours after administration of the biguanide or a pharmaceutically acceptable salt thereof is reduced by more than 65% and the method provides improvement in the patient for more than 6, 8, 10, 12, 14, 16, 18, 20, 22 or 24 hours after administration. In embodiments, provided herein are methods of treating a developmental disorder including administering to a patient in need thereof the biguanide or a pharmaceutically acceptable salt thereof which provides an in vivo plasma profile, wherein the in vivo plasma profile of the patient 10 hours after administration of the biguanide or a pharmaceutically acceptable salt thereof is reduced by more than 70% and the method provides improvement in the patient for more than 6, 8, 10, 12, 14, 16, 18, 20, 22 or 24 hours after administration.

In embodiments, provided herein are methods of treating a developmental disorder including administering to a patient in need thereof a pharmaceutical composition including a biguanide, e.g., metformin, buformin or phenformin, wherein the composition provides an in vivo plasma profile having a $C_{max}$ less than about 4 µg/ml. In embodiments, the composition provides improvement for more than 6 hours after administration to the patient.

In embodiments, the composition provides an in vivo plasma profile having a $C_{mass}$ less than about, e.g., 3.75 µg/ml, 3.5 µg/ml, 3.25 µg/ml, 3 µg/ml, 2.75 µg/ml, 2.5 µg/ml, 2.25 µg/ml, 2 µg/ml, 1.75 µg/ml, 1.5 µg/ml, 1.25 µg/ml, 1 µg/ml, 0.75 µg/ml or 0.5 µg/ml and wherein the composition provides improvement of next day functioning of the patient.

In embodiments, provided herein are methods of treating a developmental disorder including administering to a patient in need thereof a pharmaceutical composition including a biguanide, e.g., metformin, buformin or phenformin, wherein the composition provides a consistent in vivo plasma profile having a $AUC_{0-\infty}$ of less than about 13 µg·hr/ml. In embodiments, the composition provides improvement in next day functioning of the patient. In embodiments, the compositions provide an in vivo plasma profile having a $AUC_{0-\infty}$ of less than about, e.g., 12.75 µg·hr/ml, 12.5 µg·hr/ml, 12.25 µg·hr/ml, 12 µg·hr/ml, 11.75 µg·hr/ml, 11.5 µg·hr/ml, 11.25 µg·hr/ml, 11 µg·hr/ml, 10.75 µg·hr/ml, 10.5 µg·hr/ml, 10.25 µg·hr/ml, 10 µg·hr/ml, 9.75 µg·hr/ml, 9.5 µg·hr/ml, 9.25 µg·hr/ml, 9 µg·hr/ml, 8.75 µg·hr/ml, 8.5 µg·hr/ml, 8.25 µg·hr/ml, 8 µg·hr/ml, 7.75 µg·hr/ml, 7.5 µg·hr/ml, 7.25 µg·hr/ml, or 7 µg·hr/ml and wherein the composition provides improvement of next day functioning of the patient. In embodiments, the composition provides improvement in one or more symptom for more than 6 hours after administration. In embodiments, the composition provides improvement of next day functioning of the patient after administration for more than, e.g., 4 hours, 6 hours, 8 hours, 10 hours, or 12 hours, after administration of the composition to the patient.

In embodiments, provided herein are methods of treating a developmental disorder including administering to a patient in need thereof a pharmaceutical composition comprising an active substance, e.g., metformin, buformin or phenformin, wherein the composition provides an in vivo plasma profile having a $AUC_{0-\infty}$ of less than about, e.g., 6.75 µg·hr/ml, 6.5 µg·hr/ml, 6.25 µg·hr/ml, 6 µg·hr/ml, 5.75 µg·hr/ml, 5.5 µg·hr/ml, 5.25 µg·hr/ml, 5µg·hr/ml, 4.75 µg·hr/ml, 4.5 µg·hr/ml, 4.25 µg·hr/ml, or 4 µg·hr/ml. In embodiments, the composition provides improvement of next day functioning of the patient after administration for more than, e.g., 4 hours, 6 hours, 8 hours, 10 hours, or 12 hours, after administration of the composition to the patient.

In embodiments, the pharmaceutical compositions herein may be provided with conventional release, immediate release, delayed release, or extended release profiles. Conventional (or unmodified) release oral dosage forms such as tablets or capsules typically release medications into the stomach or intestines as the tablet or capsule shell dissolves. The pattern of drug release from modified release (MR) dosage forms is deliberately changed from that of a conventional dosage form to achieve a desired therapeutic objective and/or better patient compliance. Types of MR drug products include orally disintegrating dosage forms (ODDFs) which provide immediate release, extended release dosage forms, delayed release dosage forms (e.g., enteric coated), and pulsatile release dosage forms.

An ODDF is a solid dosage form containing a medicinal substance or active ingredient which disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. Patients with Angelman syndrome, Fragile X syndrome, Fragile X-associated tremor/ataxia syndrome or Rett syndrome may exhibit such behavior. Examples of ODDFs include orally disintegrating tablets, capsules and rapidly dissolving films and wafers.

Extended release dosage forms (ERDFs) have extended release profiles and are those that allow a reduction in dosing frequency as compared to that presented by a conventional dosage form, e.g., a solution or unmodified release dosage form. ERDFs provide a sustained duration of action of a drug. Suitable formulations which provide extended release profiles are well-known in the art. For example, coated slow release beads or granules ("beads" and "granules" are used interchangeably herein) in which, e.g., a biguanide such as metformin, buformin, phenformin, or a pharmaceutically acceptable salt thereof is applied to beads, e.g., confectioners nonpareil beads, and then coated with conventional release retarding materials such as waxes, enteric coatings and the like. In embodiments, beads can be formed in which the biguanide such as metformin, buformin, phenformin, or a pharmaceutically acceptable salt thereof is mixed with a material to provide a mass from which the drug leaches out. In embodiments, the beads may be engineered to provide different rates of release by varying characteristics of the coating or mass, e.g., thickness, porosity, using different materials, etc. Beads having different rates of release may be combined into a single dosage form to provide variable or continuous release. The beads can be contained in capsules or compressed into tablets. In embodiments, extended release metformin dosage forms contain 500 mg or 750 mg metformin hydrochloride as the active ingredient. In embodiments, metformin extended release dosage forms incorporate a dual hydrophilic polymer matrix system. In embodiments, metformin hydrochloride is combined with a drug release controlling polymer to form an "inner" phase, which is then incorporated as discrete particles into an "external" phase of a second polymer. After administration, fluid from the gastrointestinal (GI) tract enters the tablet, causing the polymers to hydrate and swell. Drug is released slowly from the dosage form by a process of diffusion through the gel matrix that is essentially independent of pH.

In embodiments, modified dosage forms herein incorporate delayed release dosage forms having delayed release profiles. Delayed release dosage forms can include delayed release tablets or delayed release capsules. A delayed release tablet is a solid dosage form which releases a drug (or drugs) such as a biguanide such as metformin, buformin, phenformin, or a pharmaceutically acceptable salt thereof at a time other than promptly after administration. A delayed release capsule is a solid dosage form in which the drug is enclosed within either a hard or soft soluble container made from a suitable form of gelatin, and which releases a drug (or drugs) at a time other than promptly after administration. For example, enteric-coated tablets, capsules, particles and beads are well-known examples of delayed release dosage forms. Enteric coated tablets, capsules and particles and beads pass through the stomach and release the drug in the intestine. In embodiments, a delayed release tablet is a solid dosage form containing a conglomerate of medicinal particles that releases a drug (or drugs) at a time other than promptly after administration. In embodiments, the conglomerate of medicinal particles are covered with a coating which delays release of the drug. In embodiments, a delayed release capsule is a solid dosage form containing a conglomerate of medicinal particles that releases a drug (or drugs) at a time other than promptly after administration. In embodiments, the conglomerate of medicinal particles are covered with a coating which delays release of the drug.

Delayed release dosage forms are known to those skilled in the art. For example, coated delayed release beads or granules in which, e.g., as a biguanide such as metformin, buformin, phenformin, or a pharmaceutically acceptable salt thereof is applied to beads, e.g., confectioners nonpareil beads, and then coated with conventional release delaying materials such as waxes, enteric coatings and the like. In embodiments, beads can be formed in which as a biguanide such as metformin, buformin, phenformin, or a pharmaceutically acceptable salt thereof is mixed with a material to provide a mass from which the drug leaches out. In embodiments, the beads may be engineered to provide different rates of release by varying characteristics of the coating or mass, e.g., thickness, porosity, using different materials, etc. In embodiments, enteric coated granules of as a biguanide such as metformin, buformin, phenformin, or a pharmaceutically acceptable salt thereof can be contained in an enterically coated capsule or tablet which releases the granules in the small intestine. In embodiments, the granules have a coating which remains intact until the coated granules reach at least the ileum and thereafter provide a delayed release of the drug in the colon. Suitable enteric coating materials are well known in the art, e.g., Eudragit® coatings such methacrylic acid and methyl methacrylate polymers and others. The granules can be contained in capsules or compressed into tablets.

In embodiments, a biguanide such as metformin, buformin, phenformin, or a pharmaceutically acceptable salt thereof is incorporated into porous inert carriers that provide delayed release profiles. In embodiments, the porous inert carriers incorporate channels or passages from which the drug diffuses into surrounding fluids. In embodiments, a biguanide such as metformin, buformin, phenformin, or a pharmaceutically acceptable salt thereof is incorporated into an ion-exchange resin to provide a delayed release profile. Delayed action may result from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide a delayed release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"Improvement" refers to the treatment of a developmental disorder such as Angelman syndrome, Fragile X syndrome, Fragile X-associated tremor/ataxia syndrome or Rett syndrome measured relative to at least one symptom.

"Improvement in next day functioning" or "wherein there is improvement in next day functioning" refers to improvement wherein the beneficial effect of at least one symptom lasts over a period of time, e.g., 6 hours, 12 hours, 24 hours etc.

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng·hr/ml). The area under the curve is governed by clearance. Clearance is defined as the volume of blood or plasma that is totally cleared of its content of drug per unit time (ml/min).

"Treating" or "treatment" refers to alleviating or delaying the appearance of clinical symptoms of a disease or condition in a subject that may be afflicted with or predisposed to the disease or condition, but does not yet experience or display clinical or subclinical symptoms of the disease or condition. In certain embodiments, "treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" also refers to inhibiting the disease or condition, e.g., arresting or reducing its development or at least one clinical or subclinical symptom thereof. "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic (curative) treatment are two separate embodiments of the disclosure herein.

"Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Effective amount" or "therapeutically effective amount" means a dosage sufficient to alleviate one or more symptoms of a disorder, disease, or condition being treated, or to otherwise provide a desired pharmacological and/or physiologic effect.

"Patient in need thereof" may include individuals that have been diagnosed with a developmental disorder including, for example, Autism, Angelman's syndrome, Fragile X syndrome, Fragile X-associated tremor/ataxia syndrome (FXTAS), Rett's syndrome and/or seizure disorder. The methods may be provided to any individual including, e.g., wherein the patient is a neonate, infant, a pediatric patient (6 months to 12 years), an adolescent patient (age 12-18 years) or an adult (over 18 years).

EXAMPLES

The Examples provided herein are included solely for augmenting the disclosure herein and should not be considered to be limiting in any respect.

Example 1

Bioavailability of Delayed Release Metformin

This study compared the effect of single daily doses of delayed release metformin to immediate release metformin and extended release metformin in 20 healthy volunteers. See, Buse et al., Diabetes Care, August 2015. The study was a Phase 1, randomized, four-period crossover study. The bioavailability of 1,000 mg delayed release metformin administered twice daily was ~50% that of instant release metformin and metformin extended release. A separate 12-week Phase 2, multicenter, placebo-controlled, dose-ranging study was conducted with 240 subjects having Type 2 diabetes randomized to receive metformin delayed release 600 mg, 800 mg, or 1,000 mg administered once a day; blinded placebo; or unblinded metformin extended release 1,000 mg or 2,000 mg. 600 mg, 800 mg, and 1,000 mg metformin delayed release once daily produced sustained reductions in fasting plasma glucose levels over 12 weeks compared with placebo, with an ~40% increase in potency compared with metformin extended release.

Example 2

Prospective Assessment of the Efficacy of Metformin in Patients with Angelman Syndrome This study is designed to determine whether metformin or a pharmaceutically acceptable salt thereof will lead to an improvement in one or more symptoms of Angelman syndrome. Participants are randomized into 6 separate treatment groups (A-F). Inclusion criteria for randomization will require that each participant has been previously diagnosed with Angelman syndrome by clinical evaluation or that the participant is diagnosed with one or more of the major and minor criteria for Angelman syndrome.

Major Criteria include:
Functionally severe developmental delay
Speech impairment; none or minimal words used
Movement or balance disorder
Behavioral uniqueness, frequent laughs/smiling, excitable personality, hand flapping, short attention span
Minor Criteria include:
Deceleration in head circumference growth (post-natal)
Seizures (myoclonic, absence, drop, tonic-clonic)
Abnormal EEG (with patterns suggestive of AS, or hypsarrhythmia)
Sleep disturbance
Attraction to or fascination with water
Drooling After randomization the participants are placed into 6 separate treatment groups (A-F) and a placebo group. Treatment group A receives 500 mg metformin in the morning. Treatment group B receives 850 mg metformin in the morning. Treatment group C receives 500 mg metformin in the morning and 500 mg metformin in the evening. Treatment group D receives 1000 mg metformin in the morning. Treatment group E receives 1000 mg metformin in the morning and 1000 mg metformin in the morning. Treatment group F receives 1200 mg metformin in the morning and 1200 mg metformin in the evening.

Participants are assessed throughout the treatment period to determine whether metformin administration leads to an improvement in one or more symptoms of Angelman syndrome. Several behavioral domains; communication, attention, maladaptive behaviors, and hyper-excitability are assessed. To quantify the communication behavior, participants engage in an unstructured play session to elicit speech and non-verbal communication attempts. Speech attempts by the child are transcribed phonetically and categorized into five different types of vocalizations using the *Stark Assessment of Early Vocal Development-Revised* (SAEVD-R) (Nathani, Ertmer et al. 2006) which categorizes non-speech and pre-speech sounds (protophones), as well as vowels, consonants and syllables.

Gait abnormalities occur in most cases of Angelman syndrome. Thus, five primary spatiotemporal parameters are analyzed: cadence, gait velocity, stride width, step length and percent stance. For each parameter, a principal component analysis is used to establish a gait index for assessment of the subjects.

In addition, primary outcome measures that may be assessed include changes in raw or standard scores between baseline and after trial completion of:
I. Bayley Scales of Infant and Toddler Development, 3rd edition (or the Mullen Scales of Early Learning in the more developmentally advanced subjects);
II. Vineland Adaptive Behavior Scales, 2nd edition (standard scores only);
III. Preschool Language Scale, 4th edition;
IV. Aberrant Behavior Checklist—Community version; and
V. A change from baseline in the Clinical Global Impressions Severity Scale Score.

Secondary outcome measures may include normalization of the electroencephalogram (EEG) signature when comparing post metformin administration results to baseline results.

Example 3

Prospective Assessment of the Efficacy of Metformin in Patients with Angelman Syndrome This study is designed to determine whether metformin leads to an improvement in one or more symptoms of Angelman syndrome (AS). Angelman syndrome manifests as several distinct characteristics that range in severity and include developmental delay, movement and/or balance disorder, and tremulous movement of limbs. Perhaps the most unique behavioral characteristic is the combination of a happy demeanor, smiling and frequent of bouts of laughter. Moreover, these individuals possess an easily excitable personality exhibited by hand-flapping or waving movements. Finally, these individuals suffer from severe disruptions in sleep, impairments in speech, and frequent seizures with characteristic abnormal electroencephalogram (EEG) patterns. All main domains of symptoms of AS (sleep, gross and fine motor function, behavior and communication) will be investigated, using appropriate questionnaires, diaries or actimetric data. Main focus may include motor ability and sleep. Well-established scales may be used, complemented by more innovative outcome measures for sleep and motor function. A potential confounding factor for behavior in AS is the co-existence of autism (Peters et al., Clin Genet, 2004;66[6]:530-6). At Screening, subjects may be assessed for this co-morbidity, using the Autism Diagnostic Observation Schedule (ADOS), and potentially excluded.

The primary objective of this study may be to evaluate the safety and tolerability from Baseline to Week 6 and Week 12 of metformin in adult subjects with AS across different dose levels and in two dosing schedules. The following dosing schedules may be tested against placebo: (1) Once daily (o.d.): A morning dose, titrated to the target dose of 1500 mg unless not tolerated; and (2) Twice daily (b.i.d.): morning and evening doses titrated to the target doses of 1500 mg morning dose and 1000 mg evening dose unless not tolerated.

The safety endpoints that relate to this study may include: (1) Frequency and severity of adverse events (AEs) and serious adverse events; (2) Vital signs (weight, blood pressure, temperature); (3) Laboratory parameters (electrolytes, lipids, glucose, liver and pancreas function tests, hematology, creatinine); (4) Suicidality assessed by ABC-Irritability Subscale; (5) EEG (change in background frequency, intensity of epileptiform discharges); and/or (6) Caregivers may maintain an electronic seizure diary (on same device as sleep log).

The secondary objective of this study may include the identification of a set of parameters that may best characterize the efficacy of metformin in adult AS subjects for subsequent efficacy trials. These tests may be administered at four full day site visits (Screening, Baseline, Interim and End of Treatment) by an appropriately trained professional to provide the test to an adult AS patient. Assessments may be based on direct observation and input from caregivers. The efficacy assessments that may be explored include Gross Motor Ability/Function and Fine Motor Ability/Function. Evaluation of Gross Motor Ability/Function may include analysis of spatiotemporal and functional gait measurements (Zeno Walkway and PKMAS software analysis, provided by ProtoKintetics) and Modified Performance Oriented Mobility Assessment-Gait (MPOMA-G) scale assessed while subject is walking on Zeno Walkway. Evaluation of Fine Motor Ability/Function may include analysis of Pediatric Evaluation of Disability Inventory (PEDI-CAT); ADL (to document fine motor function) and mobility domains in the content-balanced (more extensive) version.

Evaluation of sleep may include analysis by actigraphy to measure: (1) Sleep Onset Latency (SOL); (2) Total Sleep Time (TST); (3) Wake After Sleep Onset (WASO)=total # of wake epochs after sleep onset; (4) Nocturnal Awakenings (NA); and/or (5) Sleep Efficiency=total sleep time (TST) of time in bed (TIB). Additional evaluation of sleep may include analysis of parent/caregiver logs of sleep patterns that may include: (1) bed time; (2) time of sleep onset; (3) number and duration of awakenings; (4) number of disruptive behavior; (5) time of last awakening; and (6) daytime sleepiness.

This study may include three treatment groups. For example, a total of approximately 75 subjects may be enrolled and at the completion of the study, there may be approximately 25 subjects in each of the three treatment groups: 1) single morning dose 2) morning and evening dose and 3) placebo.

All subjects may receive a morning dose (either active or placebo) and an evening dose (either active or placebo) during the entire duration of treatment. For example, two dosing schedules of metformin may be tested: a single morning dose (o.d.; Schedule A) and a morning plus evening dose (b.i.d; Schedule B) designed to provide a more sustained exposure. Schedule C is morning and evening placebo. All subjects may be up-titrated to the target dose unless this target dose is not tolerated (titration conventions described below). All subjects may receive treatment for a maximum of 12 weeks at their optimal tolerated dose.

Doses may be progressively increased in 500 mg increments (active or placebo) to a target dose of 3 tablets evening dose in schedule A and B, and 2 tablets morning dose in schedule B. Each dose escalation may be performed after adequate tolerability has been assessed by caregiver and investigator. For example, treatment initiation at Day 1 with one 500 mg tablet (active (Act) or placebo (Plc)) in the evening. Then target up-titration may begin at Day 3 (window+2 days): If no adverse event (AE) related to the study drug is observed by caregiver and/or the investigator, another 500 mg tablet (active or placebo) is added in the evening. Again at Day 7 (window+2 days), Day 10 (window+2 days and Day 14 (window+2 days) if no AE related to the study drug is observed by caregiver and/or the investigator, another tablet (active or placebo) may be added in the morning. Table I below provides a graphic illustration of the titration schedule.

TABLE I

Titration Schedule

| Schedule/Time | | Days 1 to 2 | Days 3 to 6 | Days 7 to 9 | Days 10 to 13 | Day 14* |
|---|---|---|---|---|---|---|
| Schedule A | Evening | 500 mg 1 Tablet | 1000 mg 2 Tablets | 1500 mg 3 Tablets | 1500 mg 3 Tablets | 1500 mg 3 Tablets |
|  | Morning | None | None | None | Placebo 1 Tablet | Placebo 2 Tablets |
| Schedule B | Evening | 500 mg 1 Tablet | 1000 mg 2 Tablets | 1500 mg 3 Tablets | 1500 mg 3 Tablets | 1500 mg 3 Tablets |
|  | Morning | None | None | None | 500 mg 1 Tablet | 1000 mg 2 Tablets |
| Schedule C | Evening | Placebo 1 Tablet | Placebo 2 Tablets | Placebo 3 Tablets | Placebo 3 Tablets | Placebo 3 Tablets |
|  | Morning | None | None | None | Placebo 1 Tablet | Placebo 2 Tablets |

*To end of study treatment period

Slowed up-titration or delayed up-titration will be acceptable if tolerability does not allow immediate further dose-escalation at any of the above detailed days (3, 7, 10, 14). Down-titration in the case tolerability is not acceptable (e.g., somnolence, dizziness, change in behavior) after a previous up-titration step or during the course of the 12 week treatment, dose can be reduced to the previous level or even further. However, once a tolerable dose has been reached, it shall remain constant for the duration of the treatment period. Once a target dose is achieved the treatment may continue. For example, at Day 14: Earliest day the target dose can be reached (3 Tablets in the morning and 2 Tablets in the evening) the subject may be kept stable until End of Treatment visit (week 12) unless intolerability requires down-titration.

All subjects will be screened for participation in the study up to 28 days prior to the first dose administration. Inclusion criteria may include one or more of the following: (1) Age ≥18 years, ≤40 years; (2) Must possess a clinical diagnosis of AS according to the 2005 consensus criteria with developmental delay, movement or balance disorder, and speech disorder; (3) Must possess a previous or current molecular confirmation of AS; (4) Subjects must be receiving a stable dose of concomitant medications, including anti-epileptic medication, supplements, and special diets, for at least 4 weeks prior to Baseline, and be able to maintain these throughout the duration of the study.

Exclusion Criteria may include one or more of the following: (1) Non-ambulatory subjects (e.g. requiring a wheelchair) not able to perform the tests for Assessment of Motor Ability/Function (as described above); (2) Poorly controlled seizures defined as >3 absence-type seizure per week and/or >1 major seizure episodes per month; (3) Concomitant cardiovascular, respiratory diseases; Concomitant liver disease with alanine aminotransferase or aspartate aminotransferase >2.5× upper limit of normal (ULN); (4) Concomitant renal disease with creatinine above ULN (5) Concomitant hematologic disease with absolute neutrophil count >2×10$^9$/L or platelets <50×10$^9$/L or hemoglobin <80 g/L; (6) Other genetic disorders; (7) Concomitant use of minocycline, levodopa, sleep medication and any other use of any investigational agent, device, and/or investigational procedure 4 weeks prior to Baseline and during the study; (8) At risk of suicide based on ABC—Irritability Subscale Descriptive statistics may be used to summarize all primary and secondary endpoints as well as baseline variables, by treatment group. For continuous variables, n, number of missing values, mean, standard deviation, median, minimum, and maximum will be provided. For categorical variables, frequency and percentage will be presented for each category. Confidence intervals (CI) will be provided where meaningful. All CIs will be two-sided 95% confidence intervals.

Example 4

Prospective Assessment of the Efficacy of Metformin in Patients with Angelman Syndrome This study is designed to determine whether lower doses of metformin lead to an improvement in younger patients or patients with less severe clinically evaluated symptoms. For example, adolescent patients (age 10-18 years) may have the similar clinical presentation and baseline disease characteristics as the adult population but the reduction in ambulation may be less severe. In these patients it is anticipated that the target benefit of metformin will also include the reduction in ataxia and the improvement in ambulatory function.

In pediatric patients (6 months to 12 years) the diagnosis of Angelman Syndrome is usually made around 1 year of age based on important delay in the development status and eventually persistent seizures. As the child grows older, additional neurologic deficit will contribute to the disease presentation leading to ataxia and walking disability. For these prospective participants, the inclusion criteria for randomization and assessment procedures is similar to that previously described.

After randomization the participants are placed into 6 separate treatment groups (A-F) and a placebo group. Treatment group A receives 250 mg metformin in the morning. Treatment group B receives 500 mg metformin in the morning. Treatment group C receives 500 mg metformin in the morning and 250 mg metformin in the morning. Treatment group D receives 500 mg metformin in the morning and 500 mg metformin in the evening. Treatment group E receives 1000 mg metformin in the morning and 500 mg metformin in the evening. Treatment group F receives 1000 mg metformin in the morning and 1000 mg in the evening.

Example 5

Prospective Assessment of the Efficacy of Metformin in Patients with Fragile X Syndrome This study is designed to determine whether metformin leads to an improvement in one or more symptoms of Fragile X syndrome. Participants are randomized into 6 separate treatment groups (A-F). Inclusion criteria for randomization require patients that have been diagnosed with Fragile X syndrome. For example, patients who are at least moderately ill based on a Clinical Global Impression Severity score of at least 4 and have qualifying scores on the ABC-C and IQ test After randomization the participants are separated into 6 treatment groups (A-F) and a placebo group. Treatment group A receives 500 mg metformin in the morning. Treatment group B receives 850 mg metformin in the morning. Treatment group C receives 500 mg metformin in the morning and 500 mg metformin in the evening. Treatment group D receives 1000 mg metformin in the morning. Treatment group E receives 1000 mg metformin in the morning and 1000 mg metformin in the morning. Treatment group F receives 1250 mg metformin in the morning and 1250 mg metformin in the evening.

Participants are assessed throughout the treatment period to determine whether administration of metformin leads to an improvement in one or more symptoms of Fragile X syndrome. In particular, patients are assessed using one or more primary and secondary outcome measures. Primary Outcome Measures may include:

Change From Baseline in Behavioral Symptoms of Fragile X Syndrome Using the Aberrant Behavior Checklist-Community Edition (ABC-CFX) Total Score;

Global Improvement of Symptoms in Fragile X Using the Clinical Global Impression-Improvement (CGI-I) Scale;

Change From Baseline in Irritability, Lethargy/Withdrawal, Stereotypic Behavior, Hyperactivity, Inappropriate Speech and Social Avoidance Assessed by the Individual Subscales of the ABC-CFX Scale;

Change From Baseline in Repetitive Behaviors Assessed Using the Repetitive Behavior Scale—Revised (RBS-R) Scores;

Visual Analogue Scale (Behavior); Expressive Vocabulary Test; Vineland Adaptive Behavior Scale-II (VABS-II) Adaptive Behavior Composite Score; and Aberrant Behavior Checklist-Community Edition (ABC-C) Composite Score.

Example 6

Prospective Assessment of the Efficacy of Metformin in Patients with Fragile X Syndrome This study is designed to determine whether lower doses of metformin will lead to an improvement in younger patients or patients with less severe clinically evaluated symptoms. For these participants, the inclusion criteria for randomization and assessment procedures will be similar to that previously described.

After randomization the participants are randomized into 6 separate treatment groups (A-F) and a placebo group. Treatment group A receives 250 mg metformin in the morning. Treatment group B receives 500 mg metformin in the morning. Treatment group C receives 500 mg metformin in the morning and 250 mg metformin in the morning. Treatment group D receives 500 mg metformin in the morning and 500 mg metformin in the evening. Treatment group E receives 1000 mg metformin in the morning and 500 mg metformin in the evening. Treatment group F receives 1000 mg metformin in the morning and 1000 mg in the evening.

Example 7

Prospective Assessment of the Efficacy of Metformin in Patients with Fragile X-Associated Tremor/Ataxia Syndrome This protocol is directed to treating symptomatic permutation carriers who have pre-FXTAS or FXTAS symptoms including neuropathy, central pain symptoms, insomnia, and full FXTAS involving tremor and ataxia which is often associated with cognitive decline. This will be a two-site study. Participants will be individuals with the premutation and FXTAS. FMR1 CGG repeat lengths will be quantified in all subjects using conventional procedures. FXTAS will be diagnosed following published criteria (Bacalman et al., Clin Psychiatry 2006, 67:87-94; Jacquemont et al., Lancet Neurol 2003, 6:45-55). The study will involve a controlled trial of metformin lasting three months followed by a three month open-label so that those individuals that were treated for the first three months on metformin would continue for a second three months and those individuals on placebo would go on metformin for the second three months. Each site would enroll 20 patients per year for a total of 40 at each site over a two year period and between the sites there would be 80 patients participating.

Identical appearing tablets containing either metformin or placebo will be administered. After randomization the participants are randomized into separate treatment groups and a placebo group. Treatment group A receives 500 mg metformin in the morning. Treatment group B receives 850 mg metformin in the morning. Treatment group C receives 500 mg metformin in the morning and 500 mg metformin in the evening. Treatment group D receives 1000 mg metformin in the morning. Treatment group E receives 1000 mg metformin in the morning and 1000 mg metformin in the morning. Treatment group F receives 1250 mg metformin in the morning and 1250 mg metformin in the evening.

At baseline, and then at three months, and then at six months, the following studies would be done: An assessment of the severity of pain using a pain index and documentation of the type of pain; and a sleep diary will be implemented. Quantitative measures will be implemented using an actometer to observe the severity of sleep disturbances over a one week period of time. Neuropsychological measures would include the Mini-Mental State Examination (MMSE), Behavioral Dyscontrol Scale (BDS-II), Wechsler Memory Scale IV, the California Verbal Learning Test 2 (CVLT-2), Repeatable Battery for the Assessment of Neuropsychological Status (RBANS) and the SCL-90 for a determination of emotional improvements. Any improvements in the MMSE, the BDS-II, and in event related potential (ERP) studies, particularly with the N4 Repetition Paradigm, and in volumetric changes in the hippocampus will be assessed. Motor assessments will be made which documents abnormalities in those with FXTAS compared to other movement disorders. An FXTAS rating scale will be utilized. MRI volumetric studies with the 3Tesla MRI along with DTIs will be conducted. Eye-tracking measures looking at an inhibitory paradigm will be evaluated. The P6 repetition effect over a six month will be evaluated. All of these measures will be at baseline, three months, and six months. Baseline cognitive testing using the Wechsler Scale and WAIS-IV will be carried out also. This could be repeated after one year but typically not sooner. Improvement in neuropathy may be detected and followed through clinical examination using neurodiagnostic studies or electrophysiological studies.

Example 8

Prospective Assessment of the Efficacy of Metformin in Patients with Fragile X-Associated Tremor/Ataxia Syndrome This study is designed to determine whether metformin leads to an improvement in cognitive symptoms, i.e., attentional processes which are fundamental to executive function/dysfunction associated with Fragile X-associated tremor/ataxia syndrome (FXTAS) and involves a placebo-controlled, double-blind, randomized clinical trial and an auditory "oddball" task. Participants will be individuals with FXTAS. FMR1 CGG repeat lengths will be quantified in all subjects using conventional procedures. FXTAS will be diagnosed following published criteria (Bacalman et al., Clin Psychiatry 2006, 67:87-94; Jacquemont et al., Lancet Neurol 2003, 6:45-55). For the main metformin trial, 200 potential participants will be screened for eligibility. Randomization to either placebo or metformin will be blinded to all study personnel, investigators, and participants until the end of the one year trial period. Participants will participate in an auditory "oddball"/event related potentials (ERPs) experiment.

Identical appearing tablets containing either metformin or placebo will be administered. After randomization the participants are randomized into 6 separate treatment groups (A-F) and a placebo group. Treatment group A receives 500 mg metformin in the morning. Treatment group B receives 850 mg metformin in the morning. Treatment group C receives 500 mg metformin in the morning and 500 mg metformin in the evening. Treatment group D receives 1000 mg metformin in the morning. Treatment group E receives 1000 mg metformin in the morning and 1000 mg metformin in the morning. Treatment group F receives 1250 mg metformin in the morning and 1250 mg metformin in the evening.

In the auditory "oddball" experiment, patients will be instructed to detect an infrequent "oddball" tone embedded in a train of non-target standard tones. Subjects will press a button to each target detected and also keep a mental count of the number of targets in that experimental block. Prior studies in premutation carriers using the same "oddball" paradigm have demonstrated an altered frontal P300 (P3) ERP component in FXTAS patients, which tracks their executive dysfunction. See, Yang et al., Ann Neurol 74, 275-283 (2013); Yang et al., Cereb Cortex 23, 2657-2666 (2013). In these studies and others, the earlier abnormalities of prolonged N100 latency and reduced P200 (P2) amplitude were also found in a predominately male FXTAS group but not in female premutation carriers asymptomatic of FXTAS9.

Neuropsychological testing will involve examining each patient's EEG. Accordingly, EEG during a two-stimulus auditory oddball experiment will be recorded in a sound-attenuated, dimly-lit chamber. Lower (113 Hz) and higher (200 Hz) frequency pure tones will be presented at 40 dB above individual hearing level in 4 blocks, each containing 100 tones, with a stimulus onset asynchrony jittered from 1.0-1.5 seconds. Prior to each block, subjects will be instructed to respond to the infrequent (probability equaling 25%) "oddball" tones (high or low target tones, counterbalanced across blocks). A dual task will be employed in which subjects are instructed to press a button to each target tone, and to also keep a mental count of the number of targets in each block. The mental count of target tones will be reported immediately following completion after each block. 32-channel EEG will be recorded with a Nicolet-SM-2000 amplifier (band-pass=0.016–100 Hz, sampled at 250 Hz). Data Analysis will involve the |count-hit| discrepancy in each block (i.e., the absolute value of the difference between correct button-presses and mental count to target tones within a block) will be calculated for each participant, as an inverse measure (i.e., a lower value represents better performance) of attention/working memory performance during the oddball task. Event-locked EEG segments contaminated with blinks, eye movements, excessive muscle activity, or amplifier blocking will be rejected using a semi-automated computer algorithm. Artifact-free EEG segments of 1024 ms (with a 100 ms pre-stimulus baseline period, and 924 ms post-stimulus onset) will be averaged by experimental condition to obtain the ERPs. Mean amplitude and local peak latency of 4 ERP components will be quantified in the following time windows: N100 (N1, 70-150 ms), P2 (160-260 ms), N200 (N2, 170-300 ms), and P3 (300-650 ms). The waveforms to both target and standard tones will be used to measure N1. The P2 will be measured from ERPs to standard tones. The N2 component is defined from the difference wave (ERPs to targets minus standards). The P3 will be measured from both the difference wave and the ERP waveform to targets. ERP measures will be submitted to repeated-measures ANOVAs (SPSS 22, IBM) with the between-subjects factor of treatment, and the within-subjects factors of visit and electrode. Analyses of N1 and P2 will include 4 fronto-central electrodes (Fz, Cz, FC1/2). Five central channels (Cz, FC1/2, CP1/2) will be used for the N2 analyses. P3 analyses will be carried out with 26 scalp electrodes (all except FP1/2). The Greenhouse-Geiser correction will be used to adjust for violations of sphericity, where appropriate. To further characterize the modulatory effects of metformin on the P2 component, a habituation analysis will be conducted for P2 amplitude. P2 mean amplitude in response to the first 30 standard tones will be compared to the amplitude of response to the last 30 standard tones within the first block of each study, with the between-subjects factor of treatment, and the within-subjects factors of visit, trial position, and electrode. Data from a group of 16 age-matched normal controls, each of whom will have only underwent one ERP recording, will be used to demonstrate the normal habituation effect. Linear regression will be used to examine the correlations between changes (1-year follow-up minus baseline) in the |count-hit| discrepancy and in ERP measures for which significant treatment effects are shown. Correlations between local peak amplitudes of P2 (measured after application of a 30 Hz low-pass filter) and CGG repeats will be tested.

Example 9

Prospective Assessment of the Efficacy of Metformin in Patients with Rett Syndrome This study is designed to determine whether metformin or a pharmaceutically acceptable salt thereof will lead to an improvement in one or more symptoms of Rett syndrome. Participants are randomized into 6 separate treatment groups (A-F). Inclusion criteria for randomization will require that each participant has been previously diagnosed with Rett syndrome by clinical evaluation or that the participant is diagnosed with one or more of the essential and supportive criteria for Rett syndrome. Genetic testing may also be used to assist in confirming diagnosis of Rett syndrome. Of all cases of clinically diagnosed Rett syndrome, between 80-97% are found to have mutations in the MECP2 gene (a "positive" genetic test).

Essential Criteria include:
a period of normal development until between 6 to 18 months
repetitive hand movements including hand washing, hand wringing and hand clasping
a normal head circumference at birth followed by a slowing of the rate of head growth with age (starting between the time a child is 6 months and 4 years old)
significantly impaired expressive and receptive language
shakiness of the torso, which also may involve the limbs, particularly when the child is upset or agitated
unsteady, wide-based, stiff-legged gait and sometimes toe walking Supportive Criteria include:
seizures
breathing irregularities such as apnea, hyperventilation and air swallowing
abnormal sleep patterns and irritability
muscle rigidity or spasticity
irritability or agitation
electroencephalogram (EEG) abnormalities
scoliosis (curvature of the spine)
chewing and/or swallowing difficulties
teeth-grinding
decreased body fat and muscle mass
poor circulation of the lower extremities with cold and bluish-red feet and legs
decreased mobility with age After randomization the participants are placed into 6 separate treatment groups (A-F) and a placebo group. Treatment group A receives 500 mg metformin in the morning. Treatment group B receives 850 mg metformin in the morning. Treatment group C receives 500 mg metformin in the morning and 500 mg metformin in the evening. Treatment group D receives 1000 mg metformin in the morning. Treatment group E receives 1000 mg metformin in the morning and 1000 mg metformin in the morning. Treatment group F receives 1200 mg metformin in the morning and 1200 mg metformin in the evening.

Participants are assessed throughout the treatment period to determine whether metformin administration leads to an improvement in one or more symptoms of Rett syndrome. Several behavioral domains; communication, attention, maladaptive behaviors, and hyper-excitability are assessed. To quantify the communication behavior, participants engage in an unstructured play session to elicit speech and non-verbal communication attempts. Speech attempts by the child are transcribed phonetically and categorized into five different types of vocalizations using the *Stark Assessment of Early Vocal Development-Revised* (SAEVD-R) (Nathani, Ertmer et al. 2006) which categorizes non-speech and pre-speech sounds (protophones), as well as vowels, consonants and syllables.

Gait abnormalities occur in many cases of Rett syndrome. Thus, five primary spatiotemporal parameters are analyzed: cadence, gait velocity, stride width, step length and percent stance. For each parameter, a principal component analysis is used to establish a gait index for assessment of the subjects.

In addition, primary outcome measures that may be assessed include changes in raw or standard scores between baseline and after trial completion of:

VI. Bayley Scales of Infant and Toddler Development, 3rd edition (or the Mullen Scales of Early Learning in the more developmentally advanced subjects);
VII. Vineland Adaptive Behavior Scales, 2nd edition (standard scores only);
VIII. Preschool Language Scale, 4th edition;
IX. Aberrant Behavior Checklist—Community version; and
X. A change from baseline in the Clinical Global Impressions Severity Scale Score.

Secondary outcome measures may include normalization of the electroencephalogram (EEG) signature when comparing post metformin administration results to baseline results.

Example 10

Prospective Assessment of the Efficacy of Metformin in Patients with Rett Syndrome This study is designed to determine whether lower doses of metformin lead to an improvement in younger patients or patients with less severe clinically evaluated symptoms. For example, adolescent patients (age 10-18 years) may have the similar clinical presentation and baseline disease characteristics as the adult population but the reduction in ambulation may be less severe. In these patients it is anticipated that the target benefit of metformin will also include the reduction in ataxia and the improvement in ambulatory function.

In pediatric patients (6 months to 12 years) the diagnosis of Rett Syndrome is usually made after about 18 months based essential and supportive criteria discussed in Example 9. As the child grows older, additional neurologic deficit will contribute to the disease presentation leading to ataxia and walking disability. For these prospective participants, the inclusion criteria for randomization and assessment procedures is similar to that previously described.

After randomization the participants are placed into 6 separate treatment groups (A-F) and a placebo group. Treatment group A receives 250 mg metformin in the morning. Treatment group B receives 500 mg metformin in the morning. Treatment group C receives 500 mg metformin in the morning and 250 mg metformin in the morning. Treatment group D receives 500 mg metformin in the morning and 500 mg metformin in the evening. Treatment group E receives 1000 mg metformin in the morning and 500 mg metformin in the evening. Treatment group F receives 1000 mg metformin in the morning and 1000 mg in the evening.

Those skilled in the art will recognize, or be able to ascertain using no more than routine experimentation, many equivalents to the specific embodiments described herein. Such equivalents are intended to be encompassed by the claims.

What is claimed is:

1. A method of treating Fragile X syndrome comprising administering to a patient in need thereof a therapeutically effective amount of a biguanide or a pharmaceutically acceptable salt thereof, the biguanide selected from the group consisting of metformin, buformin and phenformin, wherein the method provides improvement in one or more symptoms of Fragile X syndrome in the patient.

2. The method of claim 1, wherein the patient is administered from about 50 mg to about 3000 mg metformin or a pharmaceutically acceptable salt thereof.

3. The method of claim 1, wherein the patient is administered from about 500 mg to about 2500 mg metformin or a pharmaceutically acceptable salt thereof in a 24 hour period.

4. The method of claim 1, wherein the patient is administered from about 10 mg to about 500 mg buformin or a pharmaceutically acceptable salt thereof.

5. The method of claim 1, wherein the patient is administered from about 10 mg to about 500 mg buformin or a pharmaceutically acceptable salt thereof in a 24 hour period.

6. The method of claim 1, wherein the patient is administered from about 10 mg to about 300 mg phenformin or a pharmaceutically acceptable salt thereof.

7. The method of claim 1, wherein the patient is administered from about 10 mg to about 300 mg phenformin or a pharmaceutically acceptable salt thereof in a 24 hour period.

8. The method of claim 1, wherein the in vivo plasma profile of the patient 10 hours after administration of the biguanide or pharmaceutically acceptable salt thereof is reduced by more than 50% and the method provides improvement in next day functioning of the patient.

9. The method of claim 1, wherein the in vivo plasma profile of the patient 10 hours after administration of the biguanide or pharmaceutically acceptable salt thereof is reduced by more than 50% and the method provides improvement in the patient for more than 10, 12, 14, 16, 18, 20, 22 or 24 hours after administration.

10. The method of claim 1, wherein the method provides improvement in at least one symptom selected from the group consisting of ataxia, gait, speech impairment, vocalization, cognition, motor activity, clinical seizure, subclinical seizure, hypotonia, hypertonia, feeding difficulty, drooling, mouthing behavior, sleep difficulties, repetitive hand movements, hand flapping, hand ringing, shakiness of the torso, apnea, hyperventilation and air swallowing, muscle rigidity, spasticity, teeth grinding, poor circulation of the lower extremities, easily provoked laughter and short attention span.

11. The method of claim 1, wherein the method provides improvement in the patient for more than 6 hours.

12. The method of claim 1, wherein the method provides improvement in the patient for more than 8 hours.

13. The method of claim 1, wherein the method provides improvement in the patient for at least 12 hours.

14. The method of claim 1, wherein a composition containing from about 10 mg to about 1000 mg of the biguanide or a pharmaceutical salt thereof is administered to the patient.

15. The method of claim 14, wherein a composition containing from about 500 mg to about 1000 mg of metformin or a pharmaceutical salt thereof is administered to the patient.

16. The method of claim 14, wherein the composition contains 500 mg, 850 mg or 1000 mg of metformin hydrochloride.

17. The method of claim 14, wherein the composition contains 500 mg or 750 mg of metformin hydrochloride.

18. The method of claim 14, wherein the composition is an extended release dosage form.

19. The method of claim 14, wherein the composition is a delayed release dosage form.

20. The method of claim 14, wherein the composition is an immediate release dosage form.

21. The method of claim 14, wherein the composition is a conventional release dosage form.

* * * * *